(12) United States Patent
Dannaher et al.

(10) Patent No.: US 9,788,851 B2
(45) Date of Patent: Oct. 17, 2017

(54) SURGICAL INSTRUMENT WITH TISSUE DENSITY SENSING

(75) Inventors: William D. Dannaher, Cincinnati, OH (US); Daniel W. Price, Loveland, OH (US); Cory G. Kimball, Cincinnati, OH (US); William D. Kelly, Mason, OH (US); Sora Rhee, Pennsylvania Furnace, PA (US); Jacob S. Gee, Cincinnati, OH (US); Brian D. Bertke, Fort Thomas, KY (US); Alissa L. Welling, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 13/449,837

(22) Filed: Apr. 18, 2012

(65) Prior Publication Data

US 2013/0282038 A1    Oct. 24, 2013

(51) Int. Cl.
*A61B 17/32* (2006.01)
*A61B 17/00* (2006.01)
*A61B 90/00* (2016.01)

(52) U.S. Cl.
CPC .......... *A61B 17/320068* (2013.01); *A61B 17/320092* (2013.01); *A61B 2017/00026* (2013.01); *A61B 2017/00075* (2013.01); *A61B 2017/00084* (2013.01); *A61B 2017/00119* (2013.01); *A61B 2090/065* (2016.02)

(58) Field of Classification Search
CPC .... A61B 17/320068; A61B 17/320092; A61B 2017/00026; A61B 2017/00084; A61B 2017/00119; A61B 2017/00075; A61B 2019/465
USPC ......... 606/167, 169, 205; 600/439, 442, 471
See application file for complete search history.

(56) References Cited

U.S. PATENT DOCUMENTS

| 5,980,510 A | 11/1999 | Tsonton et al. |
| 6,500,176 B1 | 12/2002 | Truckai et al. |
| 6,783,524 B2 | 8/2004 | Anderson et al. |

(Continued)

FOREIGN PATENT DOCUMENTS

| EP | 1199045 | 4/2002 |
| JP | 2007-195985 A | 8/2007 |

(Continued)

OTHER PUBLICATIONS

International Search Report dated Aug. 5, 2013 for Application No. PCT/US2013/036587.

(Continued)

*Primary Examiner* — Katherine M Shi
(74) *Attorney, Agent, or Firm* — Frost Brown Todd LLC

(57) ABSTRACT

An apparatus comprises an end effector, a body assembly, a power source, and a control module. The end effector is operable for use in a surgical procedure and can deliver energy to a surgical site. The end effector comprises at least one sensor. The sensor is able to measure at least one physical characteristic associated with the surgical site. The body assembly is in communication with the end effector. The power source is in communication with the body assembly and is operable to deliver power to the end effector. The control module is in communication with the sensor and is operable to change delivery of power to the end effector based on data from the sensor indicating a change in tissue density.

18 Claims, 10 Drawing Sheets

(56) References Cited

U.S. PATENT DOCUMENTS

| | | |
|---|---|---|
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,416,101 B2 | 8/2008 | Shelton, IV et al. |
| 7,738,971 B2 | 6/2010 | Swayze et al. |
| 7,776,027 B2 | 8/2010 | Manna et al. |
| 7,901,400 B2 * | 3/2011 | Wham et al. .................. 606/34 |
| 8,221,418 B2 * | 7/2012 | Prakash et al. ................ 606/51 |
| 9,161,803 B2 | 10/2015 | Yates et al. |
| 2001/0039419 A1 * | 11/2001 | Francischelli et al. ......... 606/42 |
| 2003/0114851 A1 * | 6/2003 | Truckai et al. ................ 606/51 |
| 2004/0034340 A1 | 2/2004 | Biscup |
| 2005/0033337 A1 * | 2/2005 | Muir et al. ................... 606/167 |
| 2006/0079874 A1 | 4/2006 | Faller et al. |
| 2006/0173480 A1 | 8/2006 | Zhang |
| 2007/0191713 A1 | 8/2007 | Eichmann et al. |
| 2007/0282333 A1 | 12/2007 | Fortson et al. |
| 2008/0058845 A1 * | 3/2008 | Shimizu ............... A61B 17/29 606/169 |
| 2008/0200940 A1 | 8/2008 | Eichmann et al. |
| 2009/0143797 A1 | 6/2009 | Smith et al. |
| 2009/0182365 A1 * | 7/2009 | Cuny ........................... 606/169 |
| 2009/0209979 A1 | 8/2009 | Yates et al. |
| 2009/0209990 A1 | 8/2009 | Yates et al. |
| 2010/0016857 A1 * | 1/2010 | McKenna et al. ............. 606/51 |
| 2010/0069940 A1 | 3/2010 | Miller et al. |
| 2011/0015660 A1 | 1/2011 | Wiener et al. |
| 2011/0082486 A1 | 4/2011 | Messerly et al. |
| 2011/0087212 A1 | 4/2011 | Aldridge et al. |
| 2011/0087218 A1 | 4/2011 | Boudreaux et al. |
| 2011/0118778 A1 * | 5/2011 | Burbank ...................... 606/205 |
| 2012/0010506 A1 * | 1/2012 | Ullrich ........................ 600/440 |
| 2012/0136279 A1 | 5/2012 | Tanaka et al. |
| 2012/0210223 A1 | 8/2012 | Eppolito |

FOREIGN PATENT DOCUMENTS

| | | |
|---|---|---|
| JP | 2007-203059 A | 8/2007 |
| JP | 2011-031048 A | 2/2011 |
| JP | 2011-087937 A | 5/2011 |
| JP | 2011-189128 A | 9/2011 |
| WO | WO 2007/069775 A1 | 6/2007 |
| WO | WO 2011/004449 | 1/2011 |
| WO | WO 2011/156310 A1 | 12/2011 |
| WO | WO 2012/044600 A2 | 4/2012 |
| WO | WO 2012/135705 | 10/2012 |

OTHER PUBLICATIONS

U.S. Appl. No. 61/410,603, filed Nov. 5, 2010.
International Preliminary Report on Patentability dated Oct. 21, 2014 and Written Opinion dated Aug. 5, 2013 for Application No. PCT/US2013/036587.
Australian Office Action dated Nov. 18, 2016 for Application No. AU 2013249514, 3 pgs.
Chinese Office Action dated Apr. 27, 2016 for Application No. CN 201380020955.7, 11 pgs.
Japanese Office Action dated Jan. 10, 2017 for Application No. JP 2015-507087, 3 pgs.

* cited by examiner

SURGICAL INSTRUMENT WITH TISSUE DENSITY SENSING

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, and issued Jun. 11, 2013 as U.S. Pat. No. 8,461,744, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued on Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, and issued Apr. 16, 2013 as U.S. Pat. No. 8,419,757, the disclosure of which is incorporated by reference herein. In addition, the surgical instruments may be used, or adapted for use, in robotic-assisted surgery settings such as that disclosed in U.S. Pat. No. 6,783,524,entitled "Robotic Surgical Tool with Ultrasound Cauterizing and Cutting Instrument," issued Aug. 31, 2004, the disclosure of which is incorporated by reference herein.

While a variety of surgical instruments have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
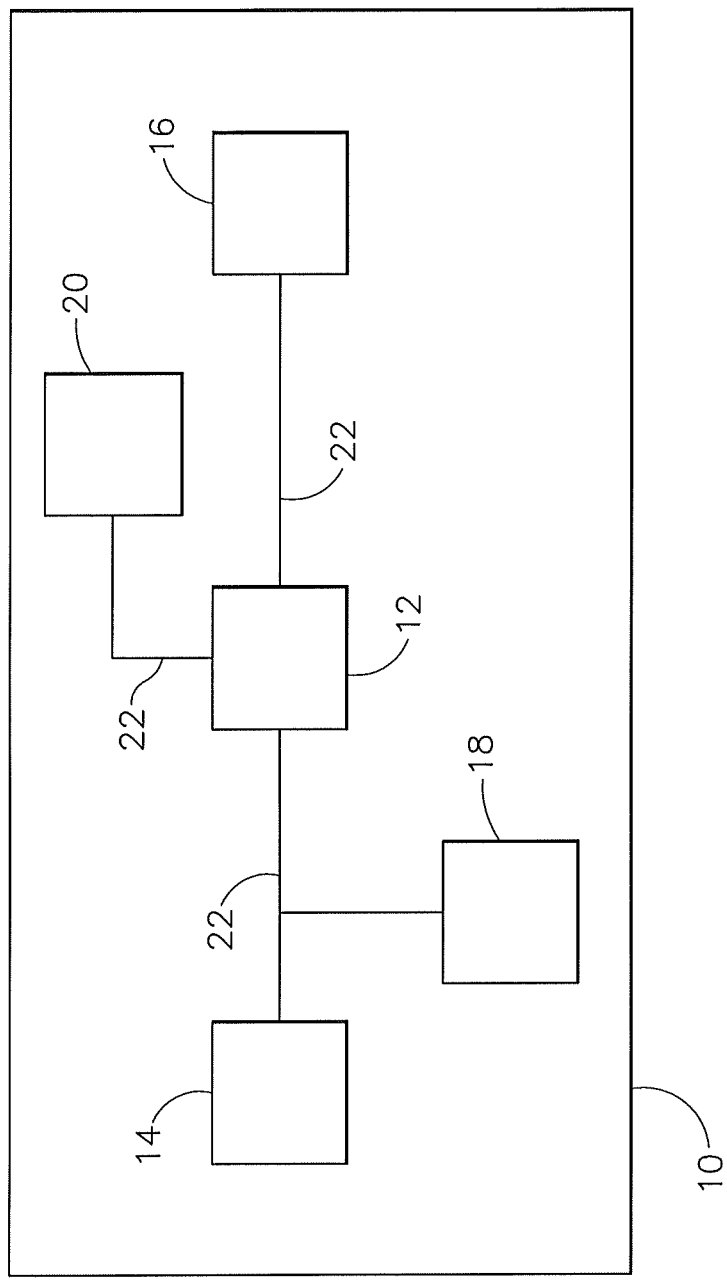
FIG. 1 depicts a block diagram view of an exemplary surgical instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Surgical Instrument

FIG. 1 shows components of an exemplary medical device and/or surgical instrument (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse. In addition or in the alternative, control module (12) may be removed for servicing, testing, replacement, or any other purpose as will be apparent to one of ordinary skill in the art in view of the teachings herein. Control module (12) may also be operable to provide pulsing energy through use of power source (14) as will be discussed further below.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired. Further detail regarding sensor (20) and variations thereof will be discussed below.

II. Exemplary Ultrasonic Surgical Instrument

Figure 2:
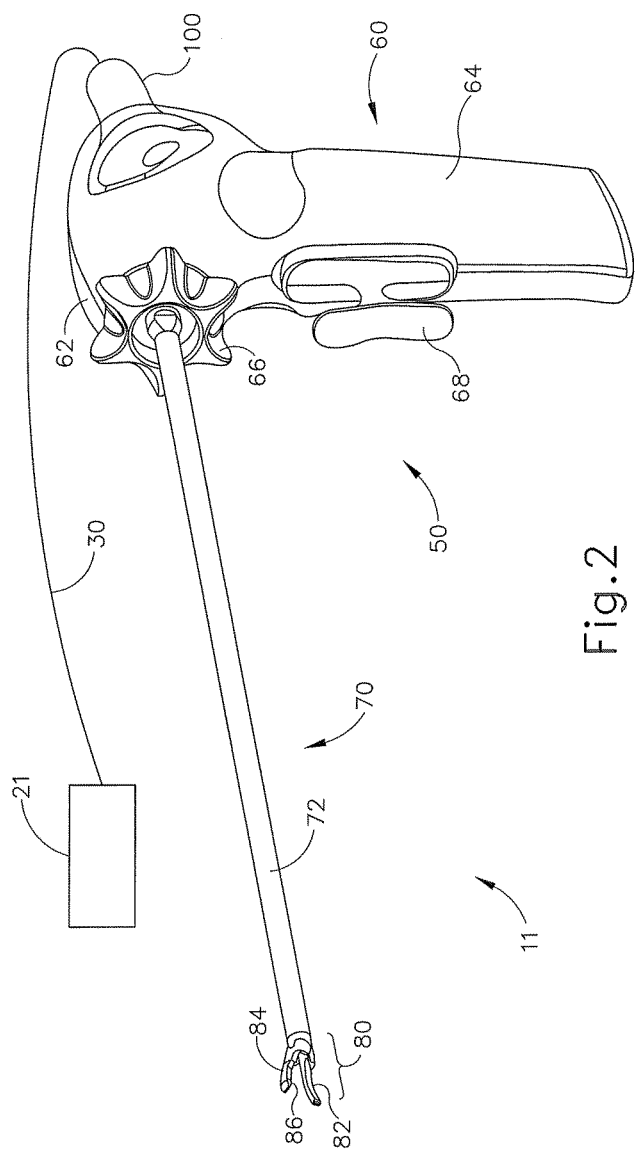
FIG. 2 depicts a perspective view of an exemplary ultrasonic surgical instrument.

FIG. 2 shows a surgical system (11), which includes an exemplary ultrasonic version (50) of instrument (10) described above. When ultrasonic components of instrument (50) are inactive, tissue can be readily gripped and manipulated, as desired, without tissue cutting. When the ultrasonic components are activated, instrument (50) permits tissue to be gripped by end effector (80) for coupling with the ultrasonic energy to effect tissue coagulation, with application of increased pressure efficiently effecting tissue cutting and coagulation. If desired, ultrasonic energy can be applied to tissue without use of the clamping mechanism of end effector (80) by appropriate manipulation of the ultrasonic blade (82).

By way of example only, surgical system (11) may be constructed and/or operable in accordance with any suitable teachings or combinations of teachings from any of the following: U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pat. Pub. No. 2009/0143797, entitled "Cordless Hand-held Ultrasonic Cautery Cutting Device," published Jun. 4, 2009, and issued Apr. 16, 2013 as U.S. Pat. No. 8,419,757, the disclosure of which is incorporated by reference herein; U.S. Pub. No. 2009/0209990 entitled "Motorized Surgical Cutting and Fastening Instrument Having Handle Based Power Source," published Aug. 20, 2009, now U.S. Pat. No. 8,657,174, issued on Feb. 25, 2014, the disclosure of which is incorporated by reference herein; U.S. Pub. No. 2010/0069940 entitled "Ultrasonic Device for Fingertip Control," published Mar. 18, 2010, now U.S. Pat. No. 9,023,071, issued on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, and issued Jun. 11, 2013 as U.S. Pat. No. 8,461,744, the disclosure of which is incorporated by reference herein. Similarly, various ways in which medical devices may be adapted to include a portable power source are disclosed in U.S. Provisional Application Serial No. 61/410,603, filed Nov. 5, 2010, entitled "Energy- Based Surgical Instruments," the disclosure of which is incorporated by reference herein.

Exemplary ultrasonic surgical system (11) comprises an ultrasonic surgical instrument (50), a generator (21), and a cable (30) operable to couple generator (21) to surgical instrument (50). A suitable generator (21) is the GEN 300 sold by Ethicon Endo-Surgery, Inc. of Cincinnati, Ohio. By way of example only, generator (21) may be constructed in accordance with the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. It should be noted that surgical instrument (50) will be described in reference to an ultrasonic surgical instrument; however, the technology described below may be used with a variety of surgical instruments, including, but not limited to, endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797 (issued Apr. 16, 2013 as U.S. Pat. No. 8,419,757). Furthermore, surgical device (50) may also be used, or adapted for use, in robotic-assisted surgery settings such as that disclosed in U.S. Pat. No. 6,783,524.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example transmission assembly (70) is configured to be an elongated, thin tubular assembly for endoscopic use, but it should be understood that transmission assembly (70) may alternatively be a short assembly, such as those disclosed in U.S. Pat. Pub. No. 2007/0282333 and U.S. Pat. Pub. No. 2008/0200940. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) coupled to the waveguide, a clamp arm (84) operable to pivot at the proximal end of transmission assembly (70), and, optionally, one or more clamp pads (86) coupleable to clamp arm (84). It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein. It should also be understood that some versions of end effector (80) may lack clamp arm (84). For instance, end effector (80) may simply include blade (82). The waveguide, which is adapted to transmit ultrasonic energy from a transducer (100) to blade (82), may be flexible, semi-flexible, or rigid. One merely exemplary ultrasonic transducer (100) is Model No. HP054, sold by Ethicon Endo-Surgery, Inc. of Cincinnati, Ohio. The waveguide may also be configured to amplify the mechanical vibrations transmitted through the waveguide to blade (82) as is well known in the art. The waveguide may further have features to control the gain of the longitudinal vibration along the waveguide and features to tune the waveguide to the resonant frequency of the system.

In the present example, the distal end of the blade (82) is disposed near an anti-node in order to tune the acoustic assembly to a preferred resonant frequency $f_o$ when the acoustic assembly is not loaded by tissue. When transducer (100) is energized, the distal end of blade (82) is configured to move longitudinally in the range of, for example, approximately 10 to 500 microns peak-to-peak, and preferably in the range of about 20 to about 200 microns at a predetermined vibratory frequency $f_o$ of, for example, 55.5 kHz. When transducer (100) of the present example is activated, these mechanical oscillations are transmitted through the waveguide to end effector (80). In the present example, blade (82), being coupled to the waveguide, oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transmission assembly (70) and transducer (100) have been described, still other suitable configurations for transmission assembly (70) and transducer (100) will be apparent to one or ordinary skill in the art in view of the teachings herein.

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). An aperture is provided on the distal end of mating housing portion (62) for insertion of various transmission assemblies (70). A rotation knob (66) is shown in the present example to rotate transmission assembly (70) and/or transducer (100), but it should be understood that rotation knob (66) is merely optional. Lower portion (64) of multi-piece handle assembly (60) includes a trigger (68) and is configured to be grasped by a user using a single hand. One merely exemplary alternative configuration for lower portion (64) is depicted in FIG. 1 of U.S. Pat. Pub. No. 2011/0015660, now U.S. Pat. No. 8,461,744, issued on Jun. 11, 2013. Toggle buttons (not shown) may be located on a distal surface of lower portion (64) and may be operable to activate transducer (100) at different operational levels using generator (21). For instance, a first toggle button may activate transducer (100) at a maximum energy level while a second toggle button may activate transducer (100) at a minimum, non-zero energy level. Of course, the toggle buttons may be configured for energy levels other than a maximum and/or minimum energy level as will be apparent to one of ordinary skill in the art in view of the teachings herein. Moreover, the toggle buttons may be located anywhere else on multi-piece handle assembly (60), on transducer (100), and/or remote from surgical instrument (50), and any number of toggle buttons may be provided. While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). The trigger portion may be operable to activate transducer (100) and may be remote from mating housing portion (62). Multi-piece handle assembly (60) may be constructed from a durable plastic (such as polycarbonate or a liquid crystal polymer), ceramics and/or metals or any other suitable material as will be apparent to one of ordinary skill in the art in view of the teachings herein. Still other configurations for multi-piece handle assembly (60) will be apparent to those of ordinary skill in the art in view of the teachings herein. For instance, instrument (50) may be operated as part of a robotic system. Other configurations for multi-piece handle assembly (60) will also be apparent to those of ordinary skill in the art in view of the teachings herein.

Still other suitable forms that system (11) may take will be apparent to those of ordinary skill in the art in view of the teachings herein.

III. Exemplary Surgical Instrument with Acoustic Sensing

It will be appreciated that as a surgical instrument (50) is used, surgical instrument (50) may encounter tissues of different densities. For instance, surgical instrument (50) may encounter different densities when transitioning between muscle, bone, fat, scar tissue, or any other type of tissue. It may be desirable to know when surgical instrument (50) encounters a change in tissue density during use of surgical instrument (50) in tissue. In some cases, it may be sufficient to know that a different tissue density is being encountered. It may also be desirable to know the nature of the different types of tissue. Furthermore, in some situations, once a different tissue density is reached it will be appreciated that it may be desirable to have surgical instrument (50) automatically change its behavior. In addition or in the alternative, the user may be notified in some manner that surgical instrument (50) is nearing or is in contact with a different type of tissue where the user may decide to manually change his/her operation of surgical instrument (50).

Figure 3:
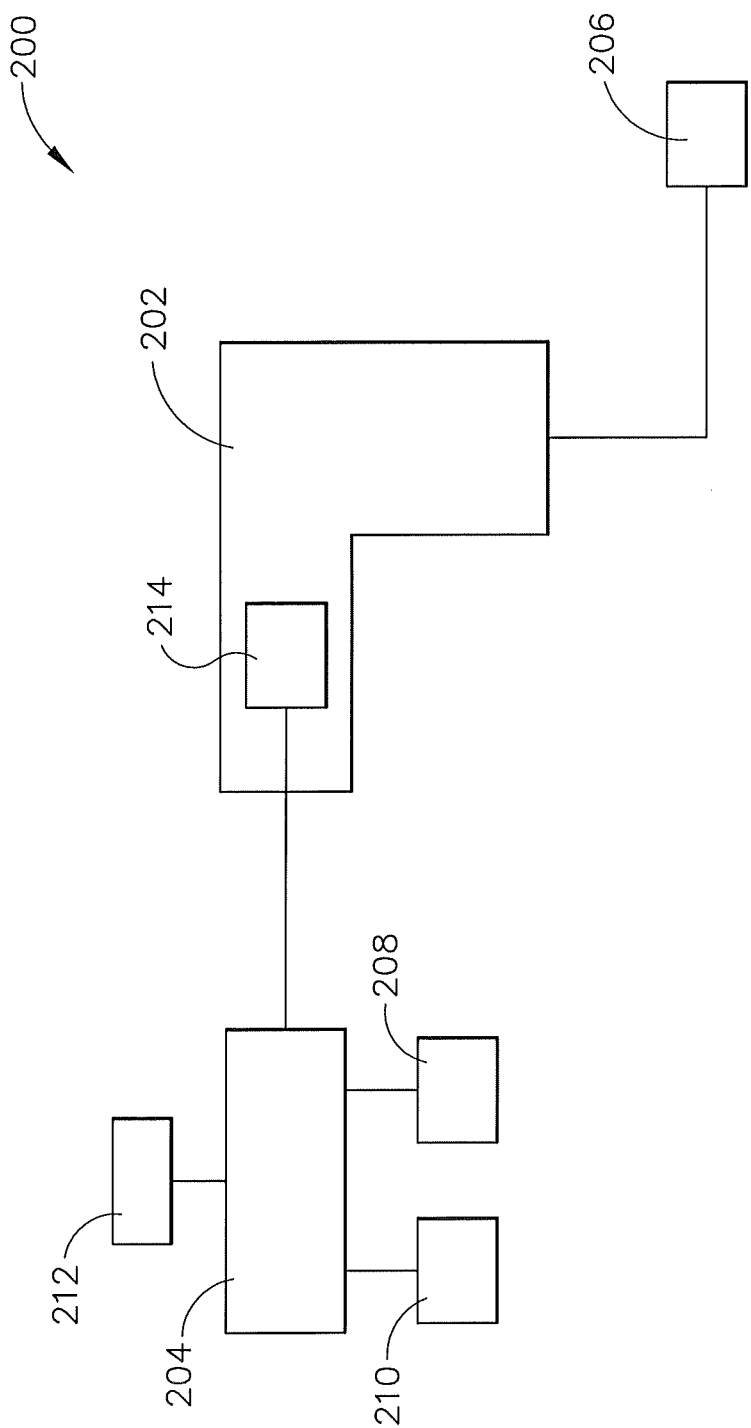
FIG. 3 depicts a block schematic of an exemplary surgical instrument.

FIG. 3 shows a schematic diagram of an exemplary surgical instrument (200) having a hand piece (202) in communication with an end effector (204). It should be understood that surgical instrument (200) is a variation of surgical instruments (10, 50) described above. End effector (204) is selectively in communication with hand piece (202), but it will be appreciated that end effector (204) in some versions may be integrally formed with hand piece (202). Other suitable configurations may be used as would be apparent to one of ordinary skill in the art in view of the teachings herein. End effector (204) comprises a variety of components including at least one microphone (210), at least one sensor (212), and at least one accelerometer (208). Of course, end effector (204) may include a variety of other components, including but not limited to, an ultrasonic blade, a clamp arm, electrosurgical features, a staple applying assembly, etc. In versions where end effector (204) includes an ultrasonic blade, end effector may lack a clamping member. For instance, end effector (204) may be configured in accordance with at least some of the teachings of U.S. Pat. Pub. No. 2008/0200940, the disclosure of which is incorporated by reference herein. Other suitable forms that a blade-only end effector (204) may take will be apparent to those of ordinary skill in the art in view of the teachings herein. In versions of end effector (204) that include an ultrasonic blade and a clamping member, end effector (204) may be configured in accordance with at least some of the teachings of U.S. Pat. Pub. No. 2007/0191713, U.S. Pat. Pub. No. 2007/0282333, and/or U.S. Pat. Pub. No. 2006/0079874, the disclosure of each of which is incorporated by reference herein. Other suitable forms that end effector (204) may take will be apparent to those of ordinary skill in the art in view of the teachings herein.

While end effector (204) of the present example comprises microphone (210), sensor (212), and accelerometer (208), it will be appreciated that end effector (204) need not necessarily contain each of microphone (210), sensor (212), and accelerometer (208). Furthermore, while FIG. 3 depicts microphone (210), sensor (212), and accelerometer (208) as being separate from end effector (204), it will be appreciated that any or all of microphone (210), sensor (212), and accelerometer (208) may be integrated into end effector (204) or in the alternative may be constructed unitarily with end effector (204). It will be understood that microphone (210) and/or accelerometer (208) could be positioned in hand piece (202). For example, microphone (210) could be positioned such that microphone (210) is operable to monitor acoustic signals at the proximal end of a harmonic waveguide in hand piece (202). Likewise, accelerometer (208) may be positioned in hand piece (202) to monitor the motion of hand piece (202) as surgical instrument (200) moves through tissue. Other suitable variations may be utilized as would be apparent to one of ordinary skill in the art in view of the teachings herein.

Microphone (210) is operable generally to act as an acoustic sensor. It should be understood that microphone (210) may be operable to detect acoustic signals at ultrasonic frequencies, auditory frequencies, and/or infrasonic frequencies. Microphone (210) in communication with a computing module (214), which will be discussed further below, is operable to detect and record sound samples of anything that might be occurring around microphone (210). For example, as surgical instrument (200) is used, it will be appreciated that parts of surgical instrument (200) may produce various acoustic signals or impulses able to indicate information regarding the nature and/or density of tissue coming in contact with surgical instrument (200). These acoustic signals or impulses may be received by microphone (210) between production of various acoustic signals or impulses; and/or may be received by alternate microphones. One example may be in the case where surgical instrument (200) guides end effector (204) through tissue of different densities, surgical instrument (200) may produce different acoustic signals based on various dampening levels or measured loss of signal strength caused by the tissue. Microphone (210) could be positioned to monitor acoustic signals at a blade or waveguide in communication with end effector (204). The type/density of tissue encountered by the ultrasonic blade may alter acoustic signal properties associated with the acoustic assembly that includes the blade. Such changes may occur at ultrasonic frequencies, auditory frequencies, and/or infrasonic frequencies. Thus, inferences on tissue density and/or type may be drawn based on the acoustic signals monitored, which may thereby provide information to the user about the type of tissue being affected by surgical instrument (200).

As noted above, microphone (210) may be operable to monitor sounds at various particular frequencies (e.g., ultrasonic frequencies, auditory frequencies, and/or infrasonic frequencies, etc.). For example, microphone (210) could be used in communication with various filters, amplifiers, etc. to focus on signals occurring at particular frequencies, thus avoiding some acoustic signals which may not provide useful information regarding surgical instrument (200). A Fast Fourier Transform (FFT) or other similar computational technique could be applied to the microphone signal to interoperate one or more frequencies being emitted from the transducer/blade resonant structure. The change in these frequencies can be used as a proxy to modal coupling and therefore as a means of detecting undesirable vibrational states or modes. Once detected, this could be used as a means of feedback to alert the user, change the behavior of the resonant system by altering the drive signal characteristics, or both. Still other suitable ways in which one or more microphones (210) may be used to detect tissue density and/or changes in tissue density will be apparent to those of ordinary skill in the art in view of the teachings herein.

Sensor (212) may include, among other things, an impedance sensor, a temperature sensor, a force sensor, and/or any other suitable type of sensor as would be apparent to one of ordinary skill in the art in view of the teachings herein. In versions where sensor (212) includes an impedance sensor, sensor (212) may be used to sense the impedance of tissue contacting end effector (204). The impedance of tissue encountered by end effector (204) may vary based on the density of such tissue. For instance, a relatively dense tissue (e.g., scar tissue) may exhibit relatively high impedance as compared to impedance exhibited by a less dense tissue (e.g., fat tissue). Thus, sensor (212) may be used to detect changes in tissue density as a function of impedance. It should be understood that such impedance may include electrical impedance and/or acoustic impedance. For instance, relatively dense tissue may exhibit both relatively high electrical impedance and relatively high acoustic impedance. It should also be understood that impedance may be measured in different ways. By way of example only, an analog circuit may be used to measure average electrical impedance by creating two voltages that are proportional to the voltage and current amplitudes (e.g., rms, peak-to-peak, or simple average) and then dividing these voltages to provide an analog voltage output that is proportional to electrical impedance. As another merely illustrative example, electrical impedance may be read and calculated digitally and instantaneously. In particular, a system may read real instantaneous voltage and real instantaneous current; then divide these values to calculate the instantaneous impedance. Various suitable ways in which an electrical impedance sensor may be implemented as sensor (212) will be apparent to those of ordinary skill in the art in view of the teachings herein. Similarly, various suitable ways in which an acoustic impedance sensor may be implemented as sensor (212) will be apparent to those of ordinary skill in the art in view of the teachings herein.

As another merely illustrative example, different tissue densities may present different thermal responses to end effector (204). Accordingly, in versions where sensor (212) includes a temperature sensor, sensor (212) may be used to detect changes in tissue density as a function of temperature. In versions where sensor (212) comprises a force sensor (e.g., a strain gauge, etc.), sensor (212) may be used to detect changes in tissue density as a function of force/strain encountered by end effector (204) as end effector (204) bears against the tissue. Still other suitable types of sensors (212) that may be used to detect tissue density and/or changes in tissue density will be apparent to those of ordinary skill in the art in view of the teachings herein.

Accelerometer (208) is operable to detect the motion of end effector (204). It will be appreciated that information gathered from accelerometer (208) may be used to determine the force with which end effector (204) moves. It will also be appreciated that a raw speed, relative speed, average speed, rate of change, or any other suitable metric associated with movement of end effector (204) may be determined. As end effector (204) encounters relatively dense tissue, this may cause end effector (204) to decelerate along its path of movement, and accelerometer (208) may be able to detect this deceleration. Similarly, end effector (204) may experience acceleration as it transitions from dense tissue to less dense tissue along its path of travel, with accelerometer (208) being able to detect this acceleration. Computing module (214) may also be able to differentiate between accelerations/decelerations that are based on changes in tissue density versus accelerations/decelerations that are based on changes in hand movements of the surgeon. For instance, computing module (214) may be able to compare data from accelerometer (208) with data from some other type of sensor (e.g., a strain gauge in handle assembly (202), etc.) to distinguish between accelerations/decelerations that are based on changes in tissue density versus accelerations/decelerations that are based on changes in hand movements of the surgeon. Still other suitable ways in which one or more accelerometers (208) may be used to detect tissue density and/or changes in tissue density will be apparent to those of ordinary skill in the art in view of the teachings herein.

A power source (206) is also in communication with handle assembly (202) and operable to deliver power to end effector (204). While the illustrated version shows power source (206) separate from handle assembly (204), power source (206) may be integrated into handle assembly (204).

Additionally, surgical instrument (200) comprises computing module (214), which is in communication with end effector (204), power source (206), accelerometer (208), microphone (210), and sensor (212). Computing module (214) may comprise any suitable components, which may include a processor, a memory, or any other suitable computing related components as will be apparent to one of ordinary skill in the art in view of the teachings herein. Computing module (214) is operable to execute or run programs or algorithms regarding the operation of any of the components of surgical instrument (200). For example, computing module (214) may be operable to control the actions of end effector (204) or of microphone (210), sensor (212), and accelerometer (208). Furthermore, computing module (214) may be in communication with power source (206) through handle assembly (204), such that computing module (214) is operable to control or utilize power source (206) to carry out any suitable routines and/or programs of computing module (214). Computing module (214) is thus operable to execute control logic.

While computing module (214) is depicted as being positioned within handle assembly (202), it will be appreciated that computing module (214) may be located in any suitable position. For example, computing module (214) may be positioned in end effector (204), in power source (206), and/or may even be contained within a module located in between handle assembly (202) and power source (206). In yet other exemplary versions, it will be appreciated that computing module (214) need not be limited to a single computing module (214). Computing module (214) may be configured such that a plurality of computing modules (214) are used where the plurality of computing modules (214) may be located in a single location or spread out across surgical instrument (200) or even remotely located.

As mentioned earlier, end effector (204) comprises a microphone (210), sensor (212), and accelerometer (208). It will further be appreciated that using end effector (204) in a surgical procedure may involve providing ultrasonic vibrations through end effector (204) to the surgical site. It will further be understood that delivering ultrasonic vibrations to a surgical site results in a tone or pitch produced by end effector (204). For example, if the vibrations are delivered from end effector (204) by an ultrasonic blade (e.g. like blade (82) described above), it will be understood that as the blade of end effector (204) travels through different types of tissue densities, vibrations from end effector (204) will produce acoustically distinct sounds since the vibrations travel at different speeds through different densities of tissue. As a result, not only are the sounds produced by the vibrations through different tissue different, it will also be appreciated that microphone (210) is operable to detect the differences in sound for when vibrations are delivered to different densities of tissue. These differences in sound can be picked up by blade (82) itself and components in acoustic communication with blade (82) and/or the waveguide. It will further be appreciated that end effector (204) may be able to deliver vibrations of different frequencies and microphone (210) may monitor acoustic signals at different frequencies. For example, by monitoring the acoustic signals at different frequencies, different data may be ascertainable. In some instances, certain changes in tissue density may be more pronounced or detectable at certain frequencies.

IV. Exemplary Methods of Using Surgical Instrument

Figure 4:
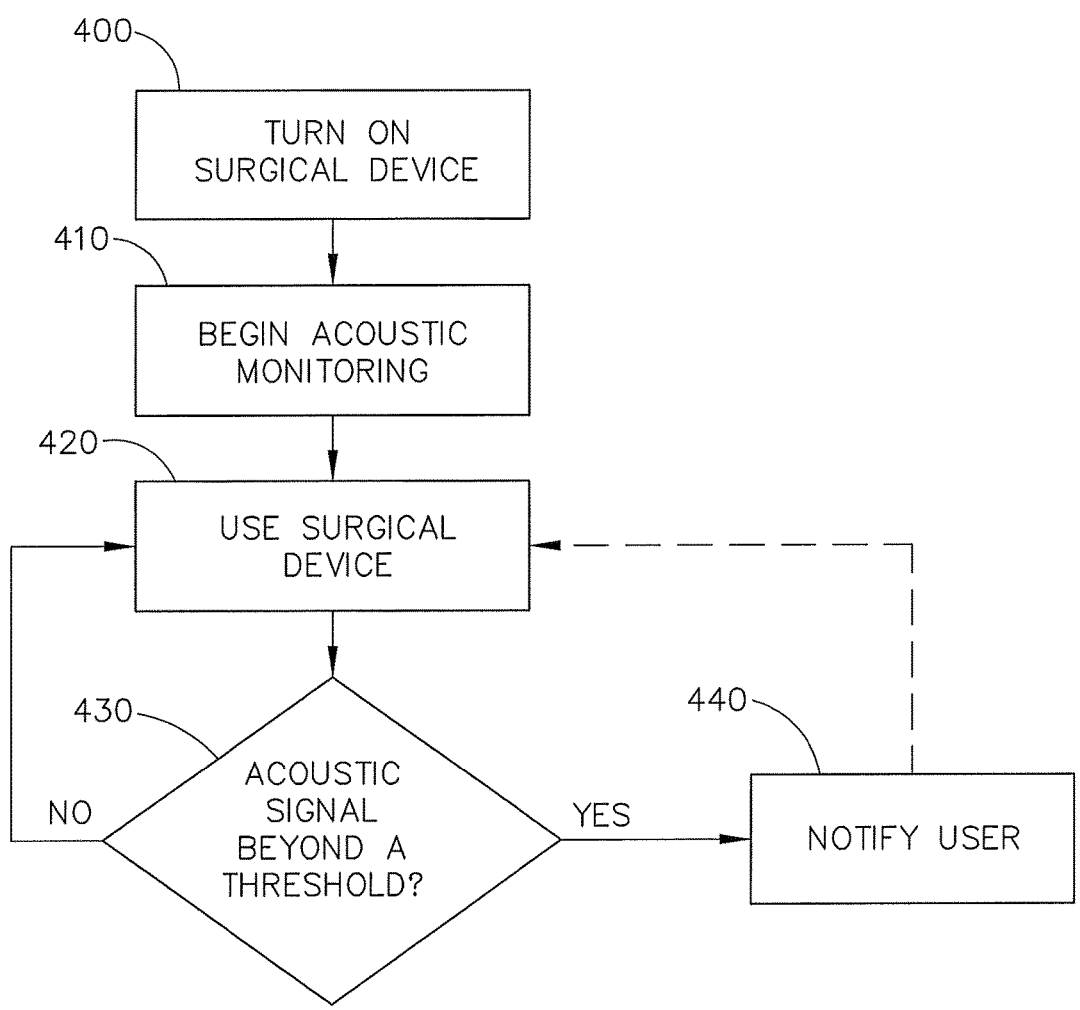
FIG. 4 depicts a flowchart diagram of an exemplary method of using the surgical instrument of FIG. 3.

FIG. 4 shows one exemplary method of using surgical instrument (200). Block (400) involves the user turning on surgical instrument (200). It will be appreciated that in some versions, surgical instrument (200) may not need to be necessarily turned on—it may default to an "on" state.

Block (410) comprises beginning acoustic monitoring. In some versions, surgical instrument (200) may be continually monitoring an acoustic signal associated with the acoustic drivetrain (e.g., ultrasonic transducer, horn, waveguide, and ultrasonic blade) of surgical instrument (200). It will be appreciated that acoustic monitoring may be carried out using microphone (210) in communication with computing module (214). Microphone (210) continually detects the audio signal associated with the acoustic drivetrain of surgical instrument (200). Computing module (214) continually receives data representing the audio signal picked up by microphone (210). It will be appreciated that acoustic monitoring may be carried out using computing module (214) while computing module (214) receives the acoustic signal. Block (420) involves the user using surgical instrument (200) at a surgical site, manipulating tissue with end effector (204). During use, block (430) continually monitors the acoustic signal to determine whether the acoustic signal exceeds a particular predetermined threshold, which can be continually updated and calculated via computing module (214).

While the present disclosure often uses the term "threshold," it is contemplated that this may include a minimum value or floor. In other words, a phrase such as "exceeding a threshold" or "exceeds a threshold," etc. as used herein may be read to also encompass situations where a value falls below a predetermined minimum value or floor in certain settings. Thus, with block (430) monitoring to determine whether the acoustic signal exceeds a particular predetermined threshold, it should be understood that this may include monitoring whether the acoustic signal falls below a predetermined minimum value or floor. It will also be appreciated that certain changes in acoustic signal (e.g., exceeding a threshold) may be indicative of a change in tissue density, which may indicate a change in tissue type. Therefore, once user is notified of the change in block (440), the user can then either stop using surgical instrument (200), continue to use surgical instrument (200), or modify the use of surgical instrument (200).

There are numerous ways in which the method depicted in FIG. 4 may be carried out, including various ways in which block (430) may be carried out. For instance, some versions of computing module (214) along with the various sensors (210, 212, 208) of end effector (204) are operable to have two monitoring modes: a transverse monitoring mode and a tissue density monitoring mode. In the transverse monitoring mode, computing module (214) is operable to perform fast Fourier transforms on acoustic samples to identify their transverse modes and associated frequencies. Computing module (214) is further operable to establish baseline modal spacing of a plurality of samples and their associated frequencies before surgical instrument (200) is used on tissue, when end effector (204) is under no load. Once a load is applied to end effector (204) during use of surgical instrument (200) in a surgical procedure, computing module (214) is operable to compare identified transverse modes to the baselines. Finally, in the event that a sensed traverse mode signal exceeds a certain threshold or falls below a floor during use of surgical instrument (200) in a surgical procedure, computing module (214) may be operable to shut down the operation of any transducers associated with surgical instrument (200) or otherwise render end effector (204) at least partially inoperable for at least a period of time.

In tissue density monitoring mode, computing module (214) is also operable to perform fast Fourier transforms on acoustic samples to identify their amplitudes at different frequencies. Computing module (214) is further operable to establish baseline amplitudes of a plurality of samples and their associated frequencies before surgical instrument (200) is used on tissue, when end effector (204) is under no load. Once a load is applied to end effector (204) during use of surgical instrument (200) in a surgical procedure, computing module (214) is operable to compare the sensed amplitude at each frequency against the pre-established baselines. Finally, in the event that the amplitude of measured frequencies drop below a predetermined range, computing module (214) is operable to convey that potentially dense tissue is being encountered by end effector (204). For instance, computing module (214) may communicate to an indicator that visually and/or audibly alerts the user that dense tissue has been encountered. Once the amplitude returns to the baseline range, then computing module (214) may communicate to the indicator to either stop alerting the user or produce a different visual and/or audible alert for the user. In addition or in the alternative to alerts, computing module (214) may affect operational characteristics of end effector (204) in response to changes in tissue density. Of course, other suitable uses and capabilities for computing module (214) will be apparent to one of ordinary skill in the art in view of the teachings herein.

Figure 5:
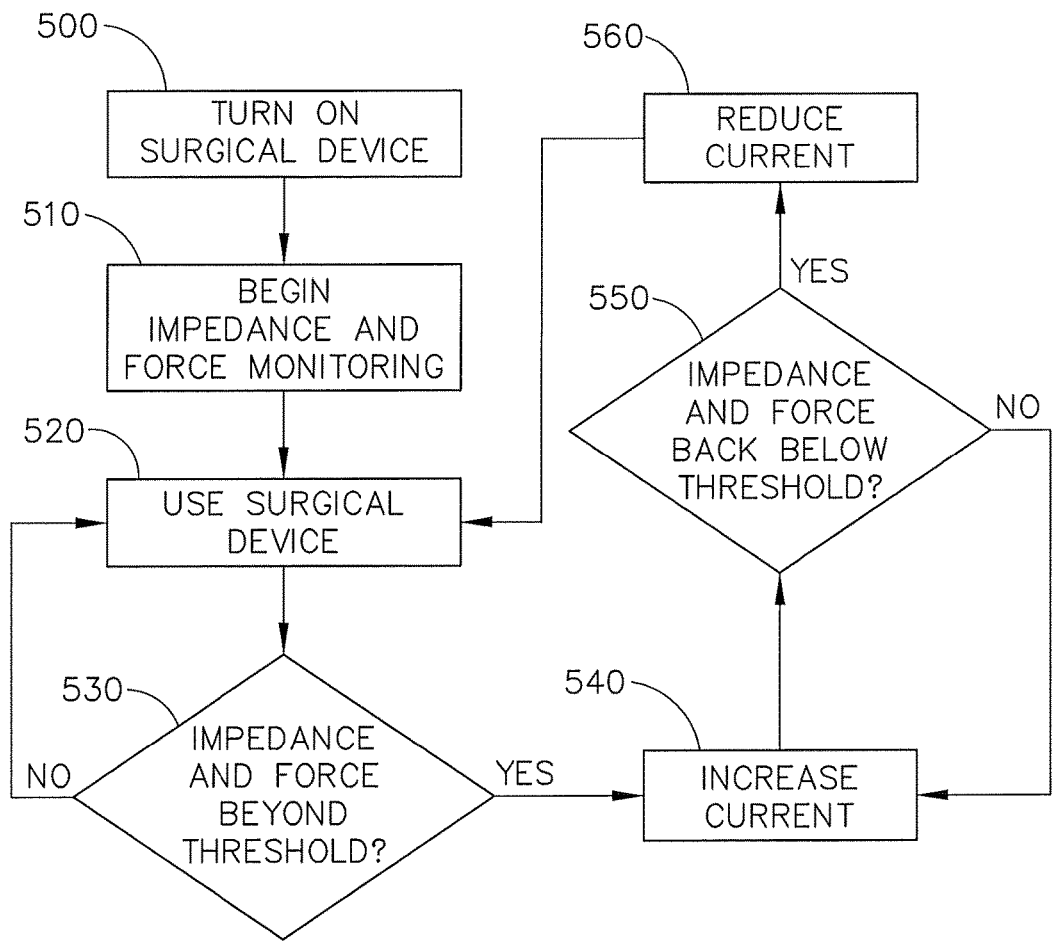
FIG. 5 depicts a flowchart diagram of an alternative exemplary method of using the surgical instrument of FIG. 3.

FIG. 5 shows another exemplary method of using surgical instrument (200). It will be appreciated that in some circumstances, surgical instrument (200) may be used in the application of abdominoplasty, body contouring of fatty tissue, and/or some other procedure where scar tissue or other dense tissue may be encountered. It will be appreciated that more current may be desirable for use with surgical instrument (200) such that scar tissue can be cut without the user noticing a change in performance of surgical instrument (200). Accordingly, block (500) shows surgical instrument (200) being turned on. Thereafter, block (510) involves beginning monitoring of tissue impedance and/or force. Impedance monitoring may be accomplished using, for example, sensor (212) of FIG. 3, which may comprise an impedance sensor configured to sense the impedance of tissue encountered by end effector (204). Furthermore, force may be measured using accelerometer (208) in conjunction with computing module (214) to sense the amount of physical resistance presented by tissue against end effector (204). While the illustrated version shows tissue impedance and/or force being monitored, it will be understood that microphone (210) may be used in addition to or in the alternative in order to monitor acoustic signals of surgical instrument (200). Block (520) then shows the user using surgical instrument (200) in a surgical procedure. During the procedure, block (530) monitors sensed impedance and force to determine whether impedance or force exceeds any particular threshold (or falls below any particular floors). In the event that either occurs, block (540) directs surgical instrument (200) to increase current through use of power source (206), thereby driving end effector (204) with greater power.

It will also be appreciated that current may be increased in response to changes in acoustic signals monitored by microphone (210). For example, a highly dampened acoustic signal may be indicative of denser tissue, which surgical instrument (200) would respond to with an increase in current. A feedback loop is created with block (550), where block (550) monitors to determine if impedance and/or force have dropped below the predetermined threshold after increasing the current in block (540). Thus, in the event that tough scar tissue is encountered by end effector (204), current will be continually increased in order to provide a smooth cutting experience to the surgeon. In the event that impedance levels, force levels, and/or acoustic signals drop back down below the predetermined threshold, then block (560) reduces current back to the level previously used at block (520).

It should be understood that selected threshold values may be dependent on several factors, including but not limited to the combination of transducer and type of end effector (204) being used, the usage habits and proficiency of the user, the type of surgical procedure being performed, and patient to patient variation in tissue. Initial thresholds may be established based on any single factor or combination of factors. In some instances, the type of end effector will be the dominant factor and this may be used in the initial setting of the threshold. This initial threshold setting may then be adjusted based on other factors. For instance, a surgeon may identify himself/herself by name and/or by entering a code that is specific to their instrument use profile. It should also be understood that the system may be a learning system where the threshold starts at a certain initial setting and is adjusted as the surgeon uses the system. In some such instances, the surgeon may start with relatively easy tissue (e.g., providing data values below the threshold) then transition to tougher tissue as the procedure progresses. This early use of instrument (200) may be used to effectively baseline the threshold early in the procedure and then allow the threshold to adjust up/down according to predetermined maximum and minimum range limits. Other suitable ways in which threshold values may be established will be apparent to those of ordinary skill in the art in view of the teachings herein.

Figure 6:
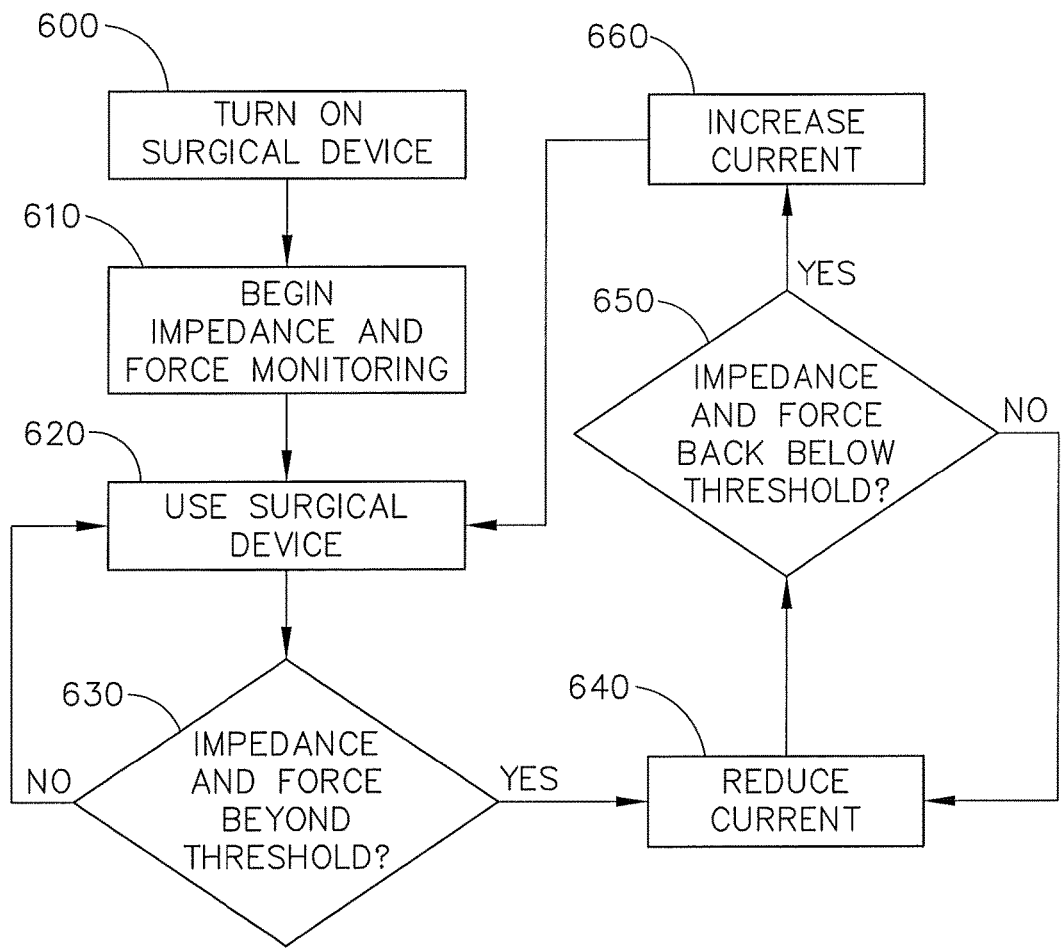
FIG. 6 depicts a flowchart diagram of yet another alternative exemplary method of using the surgical instrument of FIG. 3.

It will be appreciated that in scenarios such as applications where surgical instrument (200) is used to remove tissue from bone, it may be desirable to avoid inadvertently cutting bone in the process of removing soft tissue. Accordingly, rather than increasing current in response to a change in tissue density as was shown in FIG. 5, current may instead be decreased. To that end, block (600) of FIG. 6 shows surgical instrument (200) being turned on. Block (610) shows beginning monitoring of impedance and force. Accelerometer (208), for example, may be used to detect slowing or stopping of movement of end effector (204) through tissue. Sensor (212) may also comprise an impedance sensor used to monitor impedance of tissue encountered by end effector (204). In addition or in the alternative, block (610) could be used to monitor the acoustic signals of surgical instrument (200) to determine whether current provided to surgical instrument (200) should be decreased. In block (620), the user uses surgical instrument (200). Block (630) shows checking and continually monitoring impedance and/or force measurements to determine whether either exceeds any predetermined threshold values (or falls below any particular floors). Additionally, or in the alternative, block (630) may also monitor acoustic signals. In the event that threshold values are exceeded, it may be indicative of surgical instrument (200) encountering bone tissue. Thus, in block (640), current provided to surgical instrument (200) by power source (206) is reduced, thereby decreasing or stopping power at end effector (204). A feedback loop with block (650) is formed where block (650) continually monitors to determine whether impedance, force, and/or acoustic measurements have fallen back below a predetermined threshold. If not, then it is indicative that bone tissue may still be nearby, thus requiring less current to drive end effector (204). Once it has been determined that impedance, force, and/or acoustic measurements have fallen back below the threshold amounts, block (660) directs surgical instrument (200) to increase the current back to the level previously used at block (620).

Figure 7:
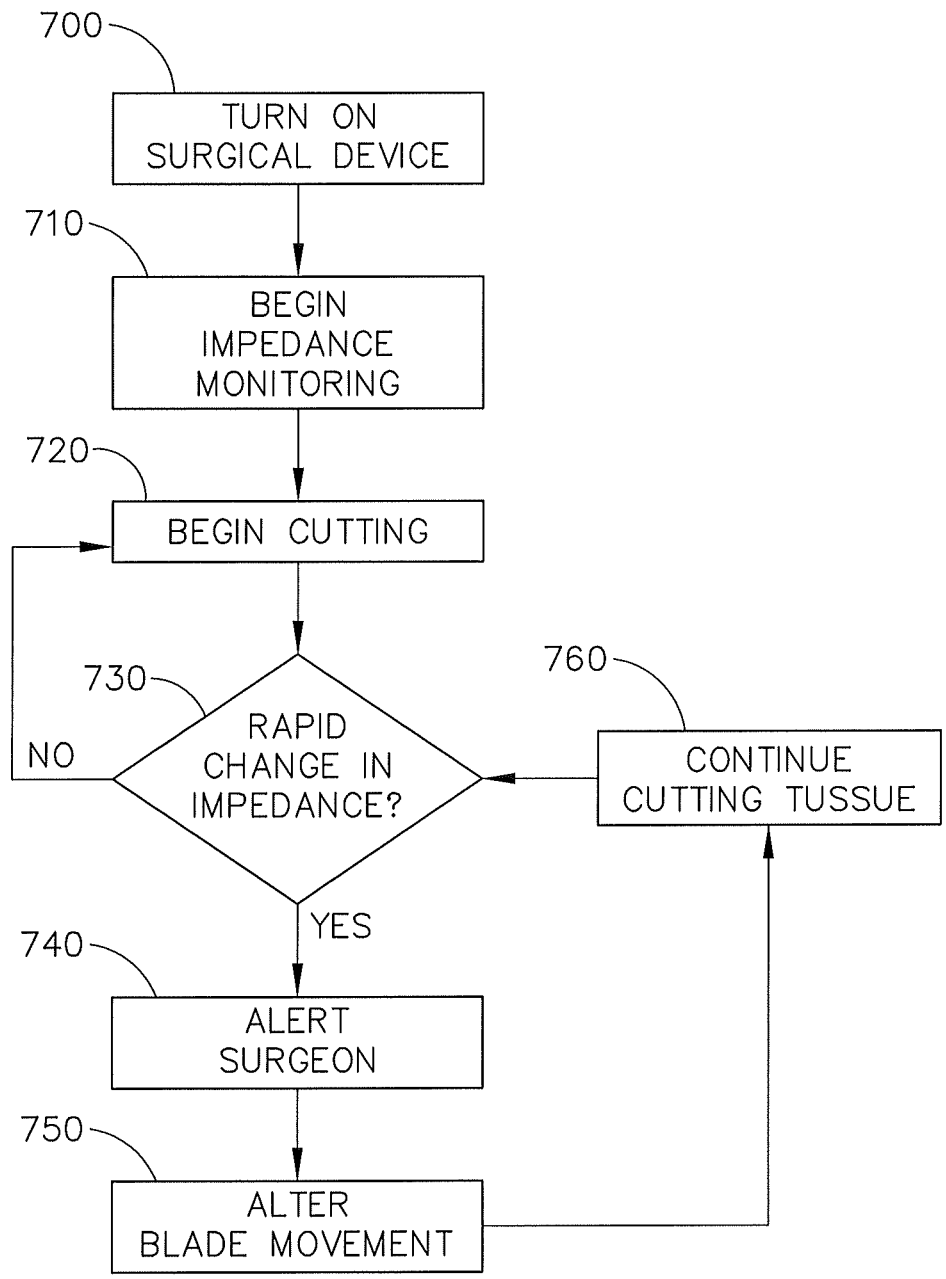
FIG. 7 depicts a flowchart diagram of yet another alternative exemplary method of using the surgical instrument of FIG. 3.

In some instances, it will be appreciated that rather than having surgical instrument (200) adjust to the sensed tissue circumstances, it may be desirable to have surgical instrument (200) simply notify the user such that the user can adjust the use of surgical instrument (200). For example, FIG. 7 shows block (700) where surgical device is turned on. Thereafter, block (710) indicates that tissue impedance monitoring begins. Tissue impedance monitoring may be accomplished through, for example, sensor (212) shown in FIG. 3. It will be appreciated that in addition to or in the alternative, acoustic signals detected through microphone (210) and/or movement detected through accelerometer (208) may be monitored as well. Thereafter, the user may begin cutting as shown in block (720). Block (730) continually monitors the tissue impedance, force, and/or acoustic signals as detected by sensor (212). In the event that a rapid change in impedance, movement of end effector (204), and/or acoustic signal occurs, block (740) alerts the user. Such an alert may comprise an audio alert, a visual alert, or any other suitable alert as would be apparent to one of ordinary skill in the art in view of the teachings herein. The alert (audio, visual, etc.) may be integrated into handpiece (202) or even power source (206), such that the user may be alerted by noticing the alert occurring on handpiece (202). In addition or in the alternative, the alert device may be noticeable from power source (206) or any other suitable location visually perceivable by the user or within earshot of the user if the alert device includes an audio alert. In block (750), the user may then alter the movement or positioning of surgical instrument (200) and thereafter continue to cut tissue as shown in block (760). For instance, the user may move end effector (204) in a reciprocating "hacksaw motion" in order to more effectively transect dense tissue. As the user moves end effector (204) through dense tissue, once the tissue becomes less dense, an alert may be provided to the user indicating that the region of dense tissue has been passed. As a result, the user may revert to using the motion for moving end effector (204) prior to the reciprocating "hacksaw motion." In the alternative, the user may change his or her motion of end effector (204) to any suitable motion as would be apparent to one of ordinary skill in the art in view of the teachings herein.

Figure 8:
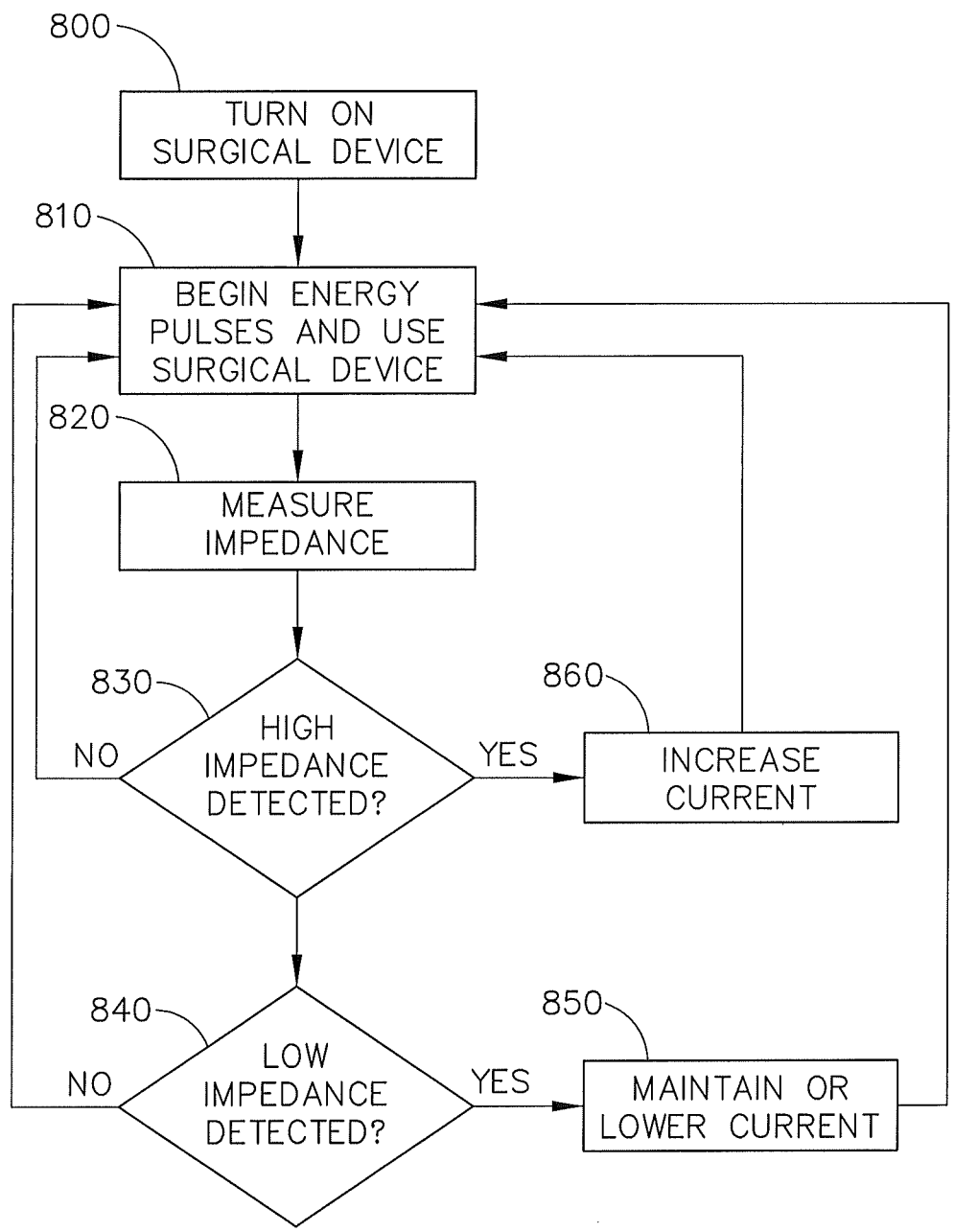
FIG. 8 depicts a flowchart diagram of yet another alternative exemplary method of using the surgical instrument of FIG. 3.

It will be appreciated that in some versions, surgical instrument (200) may need to be more flexible in the manner in which current is managed. Instead of exclusively increasing current or decreasing current, it may be desirable to use surgical instrument (200) in a manner where surgical instrument (200) can intelligently determine whether an increase in current or a decrease in current is necessary based on tissue density or changes in tissue density that end effector (204) engages. For example, in FIG. 8, block (800) involves turning on surgical instrument (200). Block (810) begins energy pulses and use of surgical instrument (200). In the case of an ultrasonic surgical instrument (50), surgical instrument (50) may deliver ultrasonic vibrations through blade (82) to the surgical site. Such vibrations may be produced by pulsing electrical power to a transducer of surgical instrument (50). In some versions, an activation pulse is delivered to transducer (100) with a frequency ranging from one pulse every 10 milliseconds to one pulse every 100 milliseconds. Of course, any other suitable pulse frequency may be used as will be apparent to those of ordinary skill in the art in view of the teachings herein. These activation pulses cause piezoelectric elements in transducer (100) to convert the electrical power into mechanical oscillatory/vibrational power, resulting in ultrasonic oscillations that are communicated along an acoustic waveguide to ultrasonic blade (82). Between the electrical activation pulses delivered to transducer (100) to produce ultrasonic vibrations, surgical instrument (50) provides a voltage to sensor (212) to detect the impedance of adjacent tissue. In the event that high impedance is detected as shown in block (830), current may be increased in the next power delivery pulse as shown in block (860) in order to assist surgical instrument (200) in cutting through relatively dense tissue at the surgical site. In the event that low impedance is detected as shown in block (840), current delivered to surgical instrument (200) in the next power delivery pulse may be maintained or lowered as shown in block (850). It will be appreciated that maintained current levels may be approximately 250 mA or any other suitable current level as would be apparent to one of ordinary skill in the art in view of the teachings herein.

In some instances, it may be desirable to determine if surgical tissue is positioned in fatty tissue or muscle tissue. It will be appreciated that the acoustic drivetrain (e.g., ultrasonic transducer, horn, waveguide, and ultrasonic blade) of surgical instrument (200) may exhibit a different resonant frequency based on whether end effector (204) is in contact with tissue such as fatty tissue versus relatively denser tissue such as muscle, which places a greater acoustic load on end effector (204). For instance, a low load such as fatty tissue may provide a relatively smaller shift in resonant frequency of the acoustic drivetrain when end effector (204) bears against the fatty tissue. Denser tissue such as muscle or cartilage may provide a higher mechanical/acoustic load against end effector (204), resulting in a relatively larger in resonant frequency of the acoustic drivetrain. These effects may be even more pronounced when end effector (204) is used as a blade instead of a shear. When end effector (204) is used as a blade, the user may determine the effective load based on the selected tissue type and the amount of pressure applied by the bladed end effector (204) against the tissue. The higher the force or pressure of application, the higher the acoustic load and the greater the shift in resonant frequency. When end effector (204) is used as a shear (e.g., through action by a clamping feature like clamp arm (84), etc.), the pressure profile may be less dependent on the amount/type of tissue between the clamping feature and the ultrasonic blade. This may enable the user to focus more on which tissue to transect and less on the nuances of the application of force to various types of tissue. In some such versions, the user may effect faster transaction times by lifting the ultrasonic blade edge into the tissue, with force sensors (212) providing measurement of pressure between the ultrasonic blade and clamping member at end effector (204).

Figure 9:
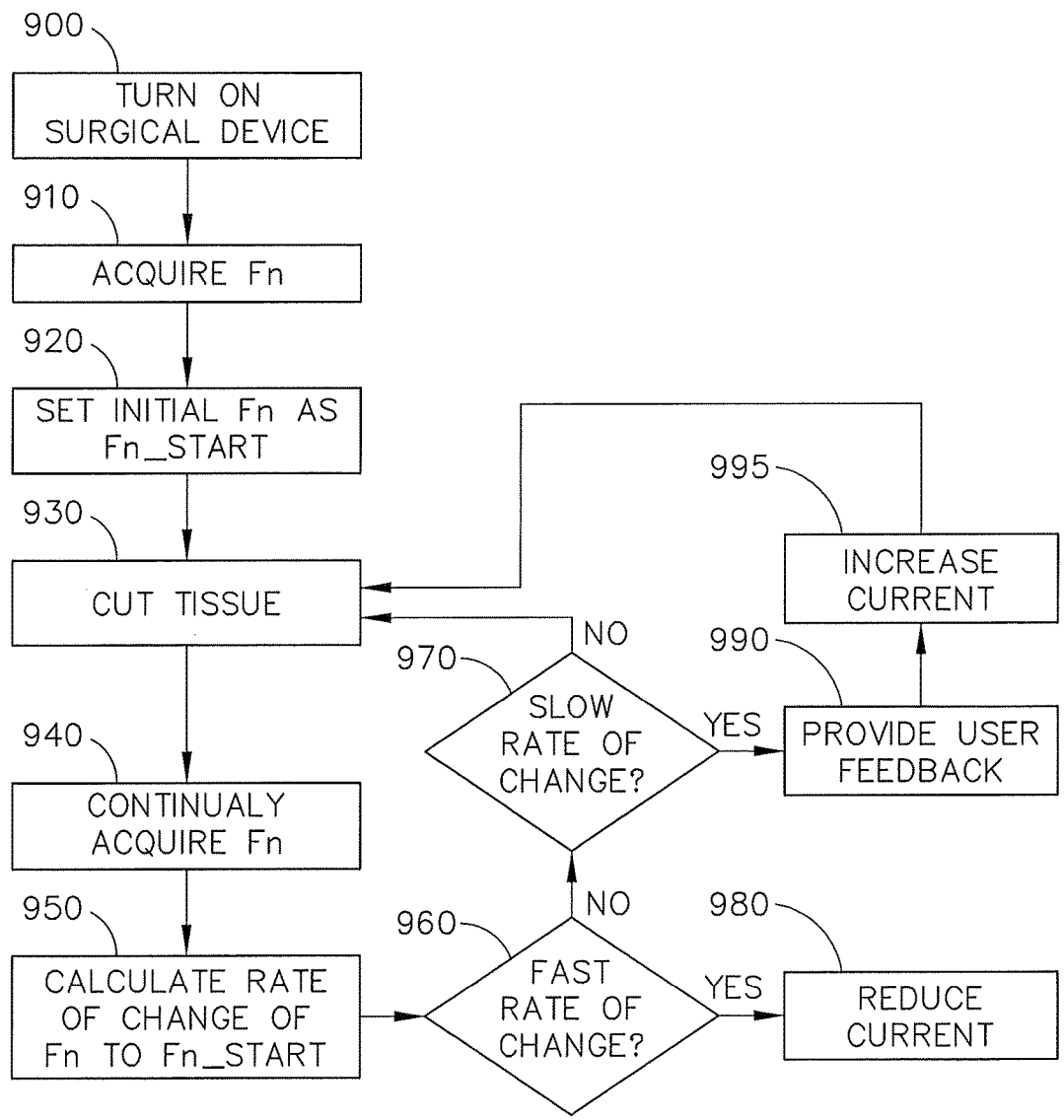
FIG. 9 depicts a flowchart diagram of yet another alternative exemplary method of using the surgical instrument of FIG. 3.

An example of processing changes in resonant frequency is shown in FIG. 9. Block (900) shows turning on surgical instrument (200). Block (910) shows determining a resonant frequency, $F_n$ followed by setting the initial frequency to $F_{n\_start}$ as seen in block (920). This establishes a baseline resonant frequency for comparison with later detected resonant frequencies. It will be appreciated that such a baseline resonant frequency ($F_{n\_start}$) may be obtained by activating an ultrasonic blade of end effector (204) before applying end effector (204) against tissue, and sensing forces at end effector (2040 with sensor (212). The user may then cut tissue as shown in block (930). As tissue is cut, sensor (212) continues to monitor the resonant frequency ($F_n$) as seen in block (940). As $F_n$ is updated, the rate of change of $F_n$ in relation to $F_{n\_start}$ is monitored to pick up shifts in the resonant frequency. In the event that a slow rate of change of $F_n$ is observed, then it can be inferred that surgical instrument (200) is in muscle tissue. The user may wish to know the presence of muscle tissue, thus block (990) provides user feedback, which may be in the form of an audible tone, vibration, or any other suitable feedback means as would be apparent to one of ordinary skill in the art in view of the teachings herein. Thereafter, current provided to surgical instrument (200) is manually or automatically increased as shown in block (995) in response to the sensed tissue density increase, to drive end effector (204) with more energy to transect the relatively dense tissue. In the event that the rate of range of $F_n$ is fast as shown in block (960), it can be inferred that surgical instrument (200) is in fatty tissue. Accordingly, current may be manually or automatically reduced as shown in block (980), to drive end effector (204) with less energy to transect the relatively soft tissue.

Figure 10:
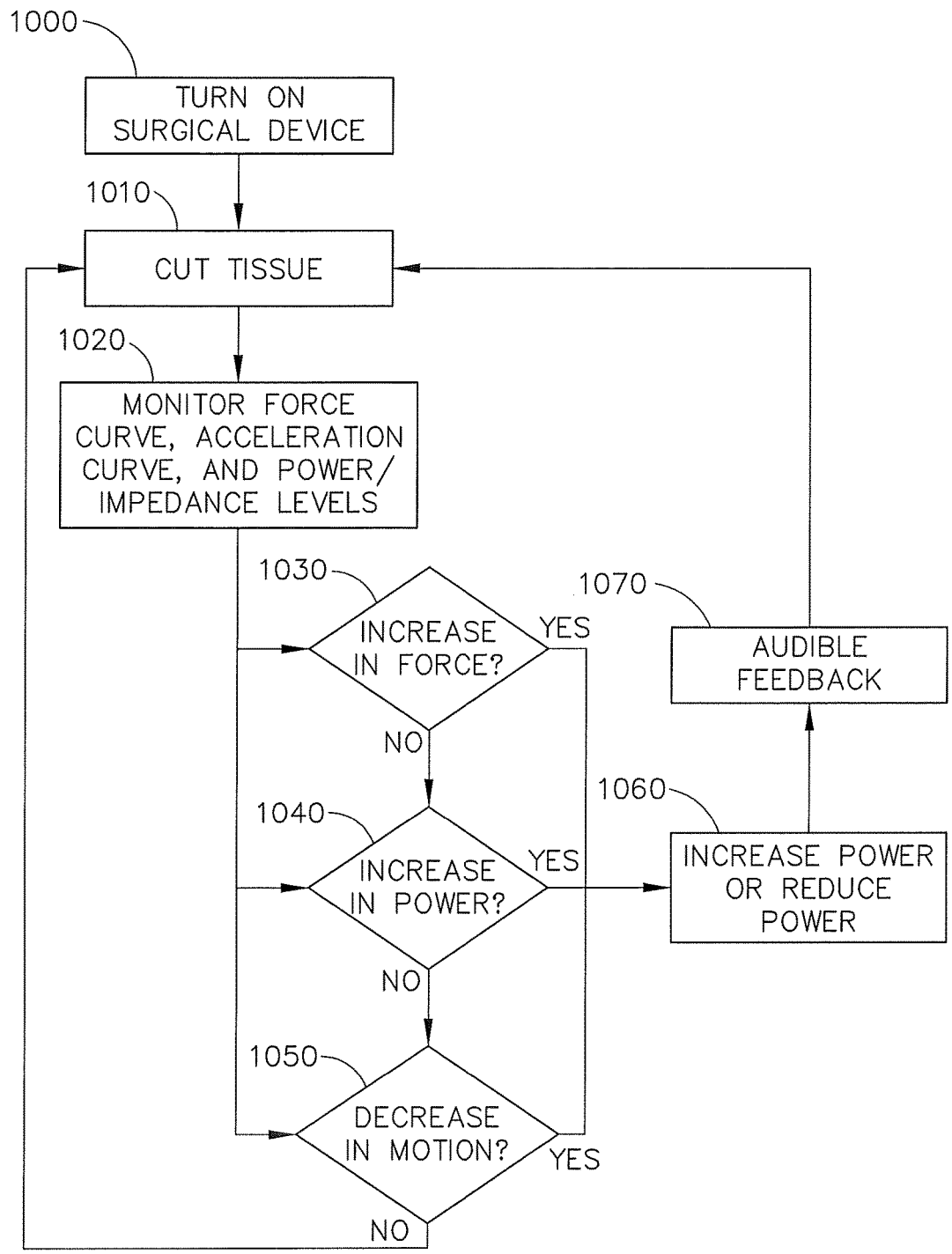
FIG. 10 depicts a flowchart diagram of yet another alternative exemplary method of using the surgical instrument of FIG. 3.

It will further be appreciated that in some cases, it may be desirable to have a surgical instrument (200) operable to simultaneously monitor several different characteristics including force changes, power/impedance changes, resonant frequency changes, and/or motion changes to determine whether the density of tissue being cut is changing. FIG. 10 shows such a system and begins with block (1000) of the user turning on surgical instrument (200). The user then uses surgical instrument (200) to cut tissue as shown in block (1010). As surgical instrument (200) is being used, force, acceleration, power, impedance, and acoustic signal levels and curves are being continuously monitored as shown in block (1020). Thereafter any increases in force as seen in block (1030) may be detected. Furthermore, increases in power as seen in block (1040) may be detected, and any decreases in motion as seen in block (1050) may be detected as well. Accordingly, current and/or power may be adjusted accordingly (increased or decreased) as shown in block (1060). For instance, block (1060) and/or block (1070) may be based on discrete values and/or trends based on various combinations of values and/or trends occurring and detected in any of blocks (1030, 1040, 1050). It will be appreciated that particular combinations of impedance values/trends and acoustic signals may be indicative of particular tissue density characteristics. Likewise, combinations of particular accelerometer values and acoustic signals may be indicative of another tissue density characteristic. It will be understood that various combinations of impedance, acoustic signals, and/or accelerometer readings may be used to indicate characteristics of tissue density, which may be programmed or otherwise integrated into computing module (214). Then accordingly, computing module (214) may be operable to provide corresponding instructions and/or orders at blocks (1060, 1070) to enable end effector (204) to continue to traverse the tissue.

Surgical instrument (200) may also be operable to specifically identify the tissue type based on monitoring in blocks (1030, 1040, 1050) and to alert the user accordingly. For example, the user may be informed that end effector (204) is engaging bone, based on a particular combination of acoustic, impedance, and/or force signals. Other combinations of signals may be used to indicate that the tissue being engaged is fatty tissue, scar tissue, etc. Thereafter, audible feedback shown in block (1070) may be provided to the user to inform the user of any tissue density change. It will also be appreciated that other feedback mechanisms such as visual feedback, tactile feedback, and/or end effector (204) control modifications may be used in addition to or in lieu of audible feedback, as will be apparent to one of ordinary skill in the art in view of the teachings herein. Furthermore, it will be appreciated that the methods discussed are merely exemplary and other suitable methods may be used as would be apparent to one of ordinary skill in the art.

In some instances where surgical instrument (200) is used through a trocar or other access port (e.g., in minimally invasive surgery), the shaft of surgical instrument (200) may be moved in a pivotal fashion about the entry point of the trocar in the patient. It should be understood that the entry point of the trocar in the patient may thus act as a virtual center of motion. Motion measured at handle assembly (202) may be proportional to the relative fulcrum (length of instrument (200) inside the patient's body/length of instrument (200) outside the patient's body). Motion, force, acceleration, etc. measured at end effector (204) may relate directly to tissue effect. Sensors located in handle assembly (202) may need to be scaled to reflect the pivot-fulcrum relationships in order to accurately represent what is happening at the interface of end effector (204) and tissue. This and other suitable ways to account for usage of instrument (200) through a trocar or other access port in a patient will be apparent to those of ordinary skill in the art in view of the teachings herein.

V. Miscellaneous

While examples above relate to surgical instrument (10) in the form of an ultrasonic instrument, it should be understood that the teachings herein may be readily applied to various types of electrosurgical instruments, including but not limited to those taught in U.S. Pat. No, 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued on Jan. 27, 2015, the disclosure of which is incorporated by reference herein; and U.S. Pat. App. No. 13/151,481, entitled "Motor Driven Electrosurgical Device with Mechanical and Electrical Feedback," filed Jun. 2, 2011, and published May 10, 2012 as U.S. Pat. Pub. No. 2012/0116379, now U.S. Pat. No. 9,161,803, issued on Oct. 20, 2015, the disclosure of which is incorporated by reference herein.

Furthermore, the teachings herein may be readily applied to various types of electrically powered cutting and stapling instruments, including but not limited to those taught in U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pub. No. 2009/0209979, entitled "Motorized Cutting and Fastening Instrument Having Control Circuit for Optimizing Battery Usage," published Aug. 20, 2009, now U.S. Pat. No. 8,662,274, issued on Jan. 7, 2014; and U.S. Pat. App. No. 13/151,481, entitled "Motor Driven Electrosurgical Device with Mechanical and Electrical Feedback," filed Jun. 2, 2011, and published May 10, 2012 as U.S. Pat. Pub. No. 2012/0116379, now U.S. Pat. No. 9,161,803, issued on Oct. 20, 2015, the disclosure of which is incorporated by reference herein. Still other suitable types of devices to which the teachings herein may be applied will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the present invention have application in conventional endoscopic and open surgical instrumentation as well as application in robotic-assisted surgery. An exemplary robotic-assist surgery system is disclosed in U.S. Pat. No. 6,783,524, entitled "Robotic Surgical Tool with Ultrasound Cauterizing and Cutting Instrument," published Aug. 31, 2004, the disclosure of which is incorporated by reference herein.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) an end effector configured for use in a surgical procedure, wherein the end effector comprises an ultrasonic blade coupled to an acoustic drivetrain, the acoustic drivetrain comprising an ultrasonic transducer, wherein the end effector is configured to deliver ultrasonic energy to a surgical site via the ultrasonic blade;
   (b) a body assembly in communication with the end effector;
   (c) a power source, wherein the power source is operable to deliver a current to the ultrasonic transducer in order to power the ultrasonic blade; and
   (d) a control module, wherein the control module is configured to determine a first resonant frequency associated with the acoustic drivetrain, wherein the control module is further configured to determine a shift from the first resonant frequency to a second resonant frequency associated with the acoustic drivetrain, wherein the control module is operable to change the current delivered from the power source to the ultrasonic transducer based on the shift from the first resonant frequency to the second resonant frequency.

2. The apparatus of claim 1, further comprising at least one sensor, wherein the at least one sensor comprises a microphone capable of performing one or more of transmitting, receiving, or measuring sound.

3. The apparatus of claim 2, wherein the microphone is configured to sense ultrasonic, auditory, or infrasonic vibrations associated with a unique modal coupling of the ultrasonic blade in an activated state.

4. The apparatus of claim 1, further comprising at least one sensor, wherein the at least one sensor comprises an impedance sensor.

5. The apparatus of claim 4, wherein the impedance sensor is configured to sense electrical impedance associated with tissue.

6. The apparatus of claim 1, wherein the end effector is operable to produce different acoustic signals based on the density of tissue proximate to or encountered by the ultrasonic blade.

7. The apparatus of claim 1, further comprising an audible feedback device in communication with the control module.

8. The apparatus of claim 1, further comprising a tactile feedback device in communication with the control module.

9. The apparatus of claim 1, further comprising at least one sensor, wherein the at least one sensor comprises an accelerometer.

10. The apparatus of claim 1, further comprising at least one sensor, wherein the control module is configured to notify the user of changes detected by the at least one sensor.

11. The apparatus of claim 1, further comprising at least one sensor, wherein the at least one sensor comprises a plurality of sensors configured to monitor different physical attributes.

12. The apparatus of claim 1, wherein the control module is programmable to have at least one predefined threshold parameter.

13. The apparatus of claim 1, wherein the control module is configured to perform simultaneous impedance and force monitoring.

14. The apparatus of claim 1, further comprising at least one sensor, wherein the control module is configured to increase power to the end effector in response to data from the at least one sensor indicating an increase in tissue density.

15. A method of detecting a change in tissue density using a surgical device having an end effector, an ultrasonic blade, at least one sensor, and a computing module, wherein the ultrasonic blade is operable to respond to at least one physical characteristic of tissue proximate to or encountered by the ultrasonic blade, the method comprising:
   (a) turning on the surgical device;
   (b) processing data from the at least one sensor with the computing module when the end effector is under no load to establish a baseline of amplitudes associated with a plurality of frequencies for the ultrasonic blade;
   (c) processing data from the at least one sensor with the computing module when the end effector is under a load to establish a first sample of amplitudes associated with the plurality of frequencies for the ultrasonic blade;

(d) comparing the first sample of amplitudes with the baseline of amplitudes associated with the plurality of frequencies, wherein the act of comparing the first sample of amplitudes with the baseline of amplitudes is performed by the computing module; and (e) simultaneously notifying a user and adjusting one or both of power or surgical technique in response to the comparison of the first sample of amplitudes with the baseline of amplitudes associated with the plurality of frequencies exceeding a threshold value, wherein the act of simultaneously notifying a user and adjusting one or both of power or surgical technique in response to the comparison is performed by the computing module.

16. The method of claim 15, wherein the act of adjusting comprises varying a current output to the end effector if the monitored physical characteristic exceeds a threshold value.

17. A method of detecting changes in tissue density using a surgical instrument with a computing module, an end effector, and a power supply, the method comprising:

(a) actuating the end effector, wherein the act of actuating the end effector produces a resonant frequency within at least a portion of the end effector;

(b) determining an initial value for the resonant frequency;

(c) using the surgical instrument;

(d) monitoring a rate of change of the resonant frequency within the end effector;

(e) determining if the rate of change deviates beyond a predetermined value; and (f) altering the amount of current produced by the power supply if the rate of change deviates beyond the predetermined value.

18. The method of claim 17, wherein the end effector comprises an ultrasonic blade, wherein the act of actuating the end effector comprises activating the ultrasonic blade and engaging the blade with tissue, wherein the tissue modifies an acoustic signal associated with the ultrasonic blade, wherein the act of monitoring rate of change of the physical characteristic comprises detecting the modification of the acoustic signal by the tissue.

* * * * *

UNITED STATES PATENT AND TRADEMARK OFFICE
CERTIFICATE OF CORRECTION

PATENT NO. : 9,788,851 B2  
APPLICATION NO. : 13/449837  
DATED : October 17, 2017  
INVENTOR(S) : Dannaher et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 182 days.

Signed and Sealed this
Nineteenth Day of June, 2018

Andrei Iancu
*Director of the United States Patent and Trademark Office*